(12) United States Patent
Wong et al.

(10) Patent No.: US 7,517,528 B2
(45) Date of Patent: Apr. 14, 2009

(54) METHOD AND COMPOSITION FOR TREATING SKIN WOUNDS WITH EPIDERMAL GROWTH FACTOR

(75) Inventors: Wan Keung Raymond Wong, Hong Kong (CN); Kat-Hon Lam, Hong Kong (CN); Man-Wo Tsang, Hong Kong (CN)

(73) Assignee: Bio-Click Technologies, Ltd., Tseung Kwan O (HK)

( * ) Notice: Subject to any disclaimer, the term of this patent is extended or adjusted under 35 U.S.C. 154(b) by 0 days.

(21) Appl. No.: 10/507,593

(22) PCT Filed: Mar. 11, 2003

(86) PCT No.: PCT/CN03/00178

§ 371 (c)(1),
(2), (4) Date: Mar. 25, 2005

(87) PCT Pub. No.: WO03/075949

PCT Pub. Date: Sep. 18, 2003

(65) Prior Publication Data

US 2005/0164924 A1    Jul. 28, 2005

Related U.S. Application Data

(60) Provisional application No. 60/363,095, filed on Mar. 12, 2002.

(51) Int. Cl.
*A61K 51/08* (2006.01)
*A61K 38/18* (2006.01)
(52) U.S. Cl. .............. 424/198.1; 424/1.45; 514/2; 514/928
(58) Field of Classification Search .......... None
See application file for complete search history.

(56) References Cited

U.S. PATENT DOCUMENTS 4,959,353 A    9/1990    Brown et al. ........... 514/12

FOREIGN PATENT DOCUMENTS

| EP | 0398619 B1 | 8/1993 |
|---|---|---|
| WO | WO 90/09782 | * 9/1990 |

OTHER PUBLICATIONS

Celebi et al. J Pharm Pharmacol. May 1994;46(5):386-7.*
Nanney, LB. Journal Invest Dermatol. 1990; 94: 624-629.*
Buckley et al. Journal Surg Res. 1987; 43: 322-328.*
Chem 405 Biochemistry Lab I, Experiment 1 Biochemical Calculations, Graphing, pH and Pipetting. Fount at: mnstate.edu/provost/Chem405_04_lab1; 11 pages total.*
Fowler et al. Home Healthc Nurse. 1999; 17: 437-44.*
Shah et al. Pharmaceutical Research, 9: 1992: 1107-1112.*
Brown et al. Plastic and Reconstructive Surgery, 88:189-196, (1991).*
Cohen et al, Plastic and Reconstructive Surgery, Aug. 1995, pp. 251-254, Topical Application of Epidermal Growth Factor onto . . . .

* cited by examiner

*Primary Examiner*—Olga Chernyshev
*Assistant Examiner*—Stacey MacFarlane
(74) *Attorney, Agent, or Firm*—Heslin Rothenberg Farley & Mesiti P.C.

(57) ABSTRACT

Epidermal growth factor (EGF) produced by an excretory recombinant approach was tested for its efficacy in treating various skin wounds. In a randomized double blind controlled study, local cream samples prepared with human EGF at a final concentration of as low as 0.02% (g/g) in topically suitable carrier were found to have an enhancing effect on the recovery of diabetes foot ulcers. This promotional effect is statistically significant and has resulted in a reduced mean healing time of over 3 weeks when compared with that of control. Both the 0.02% (g/g) and 0.04% (g/g) human EGF supplemented samples in comparison with control showed a trend of stimulatory effect when a recovery of 50% of an ulcer was considered. The EGF samples were also shown to be highly effective in promoting treatments of wounds resulting from bedsores and surgeries.

7 Claims, 19 Drawing Sheets

METHOD AND COMPOSITION FOR TREATING SKIN WOUNDS WITH EPIDERMAL GROWTH FACTOR

This is a nationalization of PCT/CN03/00178 filed Mar. 11, 2003 and published in English which in turn is based on provisional Application No. 60/363,095 filed Mar. 12, 2002.

FIELD OF THE INVENTION

This invention relates to methods and compositions for treating skin wounds using epidermal growth factor (EGF).

BACKGROUND OF THE INVENTION

The ability of EGF to accelerate the metabolism of epithelial cells and its stimulatory effect on the healing of wounds such as skin and gastric ulcers, burns and corneal injuries suggested its potential application to the treatment of diabetes foot ulcer. However, while EGF has been shown to promote healing of corneal and burn wounds at a concentration of 10 μg/ml, EGF failed to promote epithelization in wounds of patients suffering from venous stasis ulcers at the same concentration.

Diabetic foot ulcer is a major complication of diabetes mellitus. People with diabetes mellitus may have a five to fifteen times higher risk of non-traumatic amputation compared with non-diabetes. Between 1996-1998 diabetic patients accounted for 47% of all the lower limb amputations performed in a local Hong Kong hospital. In general, although some patients can be healed with traditional methods, diabetic foot ulcers can be difficult to heal in some patients and frequently lead to amputation if complicated by infection and gangrene. Several new treatment modalities such as an oxygen chamber, platelet derived growth factor (PDGF), and various local dressings have reported various degree of success. The efficacy of such methods may be relatively low, with some of such methods requiring at least 6 months for healing.

Besides diabetic foot ulcer, bedsores and large/deep surgical wounds may be difficult to heal even under medication, probably resulting from the large areas involved. If these wounds are not treated in time, they will deteriorate and subsequently may become incurable and life threatening. Therefore, an effective medical treatment may not only help the patients recover from these skin complications, but may also lead them to a better quality of life, reduced medical care or expense, or even a prolonged life span. Unfortunately, current treatment methods may not be able to provide a relatively effective method to such large-area wounds.

OBJECT OF THE INVENTION

Therefore, it is an object of this invention to resolve at least one or more of the problem as set forth in the prior art. As a minimum, it is an object of this invention to provide the public with a useful choice.

SUMMARY THE INVENTION

Accordingly, this invention provides, in the broad sense, a method and the corresponding composition for treating skin wounds using EGF as the active ingredient.

In one aspect of this invention, a method for treating skin wounds is provided, which comprises the step of topically administering a composition to the skin wounds, said composition including a topically effective amount of epidermal growth factor (EGF) and a topical acceptable carrier.

Another aspect of this invention provides a composition for treating skin wounds including a topically effective amount of epidermal growth factor (EGF) and a topical acceptable carrier.

BRIEF DESCRIPTION OF THE DRAWING

Preferred embodiments of the present invention will now be explained by way of example and with reference to the accompany drawings in which.

DETAIL DESCRIPTION OF PREFERRED EMBODIMENTS

Figure 1:
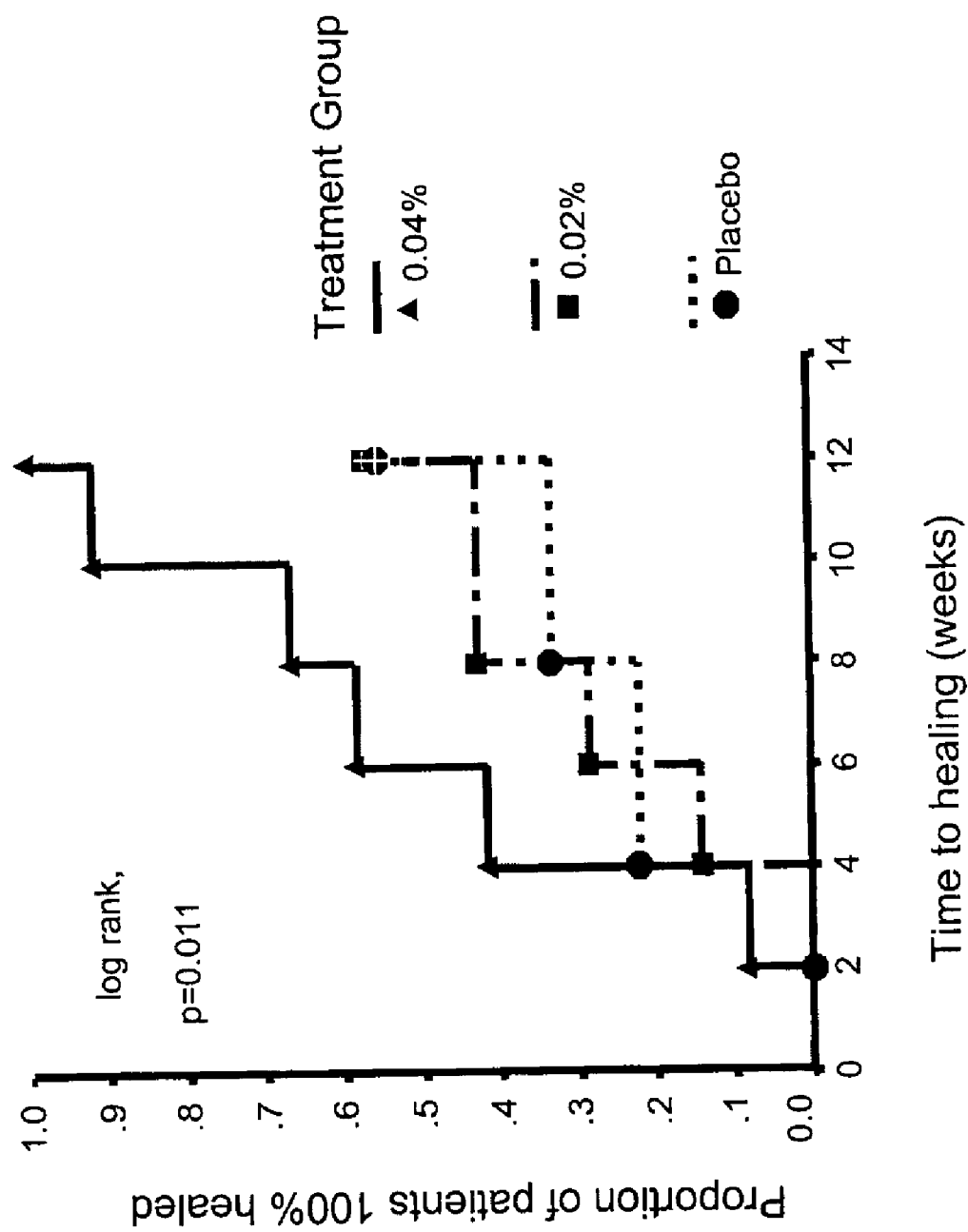
FIG. 1 shows the mean healing times (100% healing) expressed in survival function plots of Groups 1-3 patients being treated by the compositions of this invention containing different amounts of EGF.

This invention is now described by ways of example with reference to the figures in the following sections.

This invention relates to the application of a composition containing at least 0.02% (g/g) EGF and a topically acceptable carrier to the skin wound of a patient which resulted in unexpected positive healing effects. At the very least, the time required for 50% healing, in which the area of the shin wound is reduced by 50%, is substantially reduced compared with existing methods. The study of this invention found that using a composition containing 0.02% (g/g) or 0.04% (g/g) of EGF may reduce the time required to achieve 50% healing by 2-4 weeks. In the case of treating burns, it was found that even 0.001% (g) of EGF may be effective in accelerating wound healing.

Although using 0.02% (g/g) EGF in the composition of this invention was found to be effective in achieving 50% healing, it was also found that it may fail to achieve totally healing in some cases. On the other hand, when EGF is used in an amount of 0.04% (g/g), totally healing was observed in some patients after 4 weeks of treatment, and all of the patients were totally healed after 12 weeks. It was also found that when EGF is used in an amount of 0.03% (g/g), the results are almost indistinguishable from those using 0.04% (g/g) of EGF. Further details will be described in the following examples.

In one embodiment of this invention, the patient may first be with the composition containing 0.02% (g/g) EGF to achieve 50% healing, and then treated with the composition containing 0.04% (g/g) EGF to achieve total healing. Although this may be more economical than using 0.04% (g/g) EGF alone as less amount of EGF may be required, the complication may be less preferred in some cases.

Naturally, human EGF (hEGF) is preferred to be used in the method and composition of this invention when treating human. The structure of hEGF is well documented and can at least be found in "Epidermal Growth Factor and Transforming Growth Factor alpha (by King et al in: Physiology, Biochemistry, and Molecular Biology of the Skin, L. A. Goldsmith, ed.) 2nd edition, Vol. 1, pp. 329-350. Oxford University Press, N.Y.) and Proceedings of the 10th Americal Peptide Symposium by Han et al. (in: Peptides, Chemistry and Biology, (G. R. Marshall, ed.), pp 581-583. Escom, Leiden). However, if such are used to treat other mammals, it may be preferable to use EGF endogenous to the mammals, being treated.

The following may be the requirements on the topical acceptable carrier used in the invention:
1. non-toxic; and
2. the EGF will remain stable and bio-available when applied directly to the skin wound.

The EGF can be dissolved in a liquid, dispersed or emulsified in a medium in a conventional manner to form a liquid preparation or is mixed with a semi-solid (gel) or solid carrier to form a paste, powder, ointment, cream, lotion or the like for easy application to the skin. The choice of the final form may be decided in terms of convenience.

Although further description of the carrier may not be necessary to one skilled in the art, some suitable carriers will now be listed. These may include topically acceptable liquids, creams, oils, lotions, ointments, gels, or solids, such a conventional cosmetic night creams, foundation creams, suntan lotions, sunscreens, hand lotions, make-up and make-up bases, masks and the like. The compositions can contain other optional suitable ingredients estrogen Vitamin A, C and E, alpha-hydroxy of alpha-keto acids such as pyruvic, lactic or glycolic acids, lanolin, vaseline, aloe vera, methyl or propyl paraben, pigments and the like. Suitable topically acceptable carriers include water, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, collagen, starch, or gum arabic, synthetic polymers, such as discussed below, alcohols, polyols, and the like. Preferably, the carrier is a water miscible carrier composition that is substantially miscible in water. Such water miscible topical cosmetically acceptable carrier composition can include those made with one or more appropriate ingredients set forth above but can also include sustained or delayed release carrier, including water containing, water dispersable or water soluble compositions, such as liposomes, microsponges, microspheres or microcapsules, aqueous base ointments, water-in-oil or oil-in-water emulsions, gels or the like.

EXAMPLES

This invention is now illustrated by the following examples, which shall not be interpreted as limiting.

Example 1

Group Study of Diabetes Foot Ulcer

Methods and Patients

A randomized double-blind controlled trial was conducted to study the efficacy of human epidermal growth factor hEGF) in promoting diabetic foot ulcer healing with 88 patients. Predetermined criteria were used for patient selection, they were; ulcer grade 1-2, ulcer located below the ankle, adequate perfusion as indicated by an ankle brachial-index of $\geq 0.7$. Patients were excluded if: sugar control was very poor (HbAlc$\geq$12%), or had severe grade ulcers ($\geq$3). Initial assessment and standard wound care and debridement was given as in an ordinary diabetic foot clinic. The patients were reviewed two weeks later. In the second consultation, patients whose ulcer healed more than 25% with conventional foot ulcer care were excluded. Informed consent was obtained from the remaining patients and randomization was done by drawing envelopes, although the patients were blind to the concentrations of hEGF during the experiments. The final candidates were randomly assigned into three groups:
1. Group 1 were treated with Acetovegin® 5% cream alone, which has the following compositions as indicated in the package of the cream: 1 g of cream contains 2 mg (corresponding to dry mass) of deproteinized hemoderivative of calf blood, and 0.2 mg of benzalkonium chloride. There was no particular reason in choosing Acetovegin® 5% cream as the control other than this cream was available at the clinic where the experiments were conducted.
2. Group 2 patients were treated with Acetovegin® 5% cream (with composition as stated above) plus 0.02% (g/g) hEGF.
3. Group 3 patients were treated with Acetovegin® 5% cream (with composition as stated above) plus 0.04% (g/g) hEGF.

All patients were followed up on a biweekly bass for wound care and debridement and trimming of keratosis. Antibiotic would be given if it was infected as indicated by purulent discharge or by positive bacterial culture. Photos of the wound's size were being taken for computer measurement and comparing with a reference area having a known size.

Local application of study cream was applied and covered with sterile gauze. Patients were instructed to have daily normal saline dressing and local application of cream in the government out-patient-clinic or community nurse would be asked to have home visit for those with ambulatory problem.

Wound parameters, such as exudates sign of infection granulation tissue and eschar were documented in each visit and complete healing was defined as full epithelialization of the wound with absence of discharge.

Statistical Analysis

Analysis was based on intention to treat and Kaplan Meier survival analysis was employed to compare the healing rate between different groups. One way ANOVA was used for clinical parameters analysis. If more than one wound was present in one patient the total areas of the ulcers was taken together and treated as one single wound.

Results:

Among the 88 patients admitted to the experiments, 56 patients were excluded for various reasons: 23 (41%) because their ulcers healed more than 25% in the second visit with conventional treatments. 19 (33.9%) had ankle-brachial-index; <0.7, 5 (8.9%) had high grade foot ulcer; 5 (8.9%) refused because of social reason; 2 (3.6%) had poor diabetes control; another 2(3.9%) had ulcer above malleoli.

Of the 30 patients that suffered from unhealed ulcers they were randomly assigned into 3 groups as stated above: Group-1 (9/30), the control, was treated with Acetovegin® 5% cream alone; Group-2,(9/30) was treated with Acetovegin® 5% cream plus 0.02% (g/g) hEGF; Group-3, (14/32) Acetovegin® 5% cream plus 0.04% (g/g) hEGF. The end point of a treatment was defined as complete closure of the wound, whereas failure to heal was defined as incomplete healing after 12 weeks of treatment.

Upon subsequent follow up, one patient from Group-1 was excluded before completion of study because of relapse of a pysehictric symptom and poor compliance (She had four ulcers over dorsum of her feet. Two of the ulcers healed before she was excluded). One patient from Group-3 was excluded because of poor personal hygiene (she had five ulcers over dorsum and sole of her feet. Four of the ulcers healed before she was excluded at week-8). Final analysis consisted of 28 patients with 37 ulcers. The baseline characteristics were depicted in Table 1. There were more female patients in Group-3. Other clinical parameters were of no statistical difference among the groups. By the end of 12 weeks, four patients from Group-1, five patients from Group-2 and all patients from Group-3 healed with a healing rate 57%, 55% and 100%, respectively.

FIG. 1 shows the mean 100% healing times in Group 1, Group 2 and Group 3 patients were 9.79±1.24 weeks (confidence interval (C.I.) 7.35-12.21), 9.43±1.38 weeks (C.I. 6.73-12.13) and 6.67±0.93 weeks (C.I.4.84-8.49), respectively. Test statistics for equality of survival distributions (log rank) is 9.00 with a df of 2 and a significance of 0.0111. Further statistical data of FIG. 1 is shown in Table 2. It can be observed that Group 3 patients took at least an average of 3 weeks less than the other two groups to heal and this difference was statistically significant.

Figure 2:
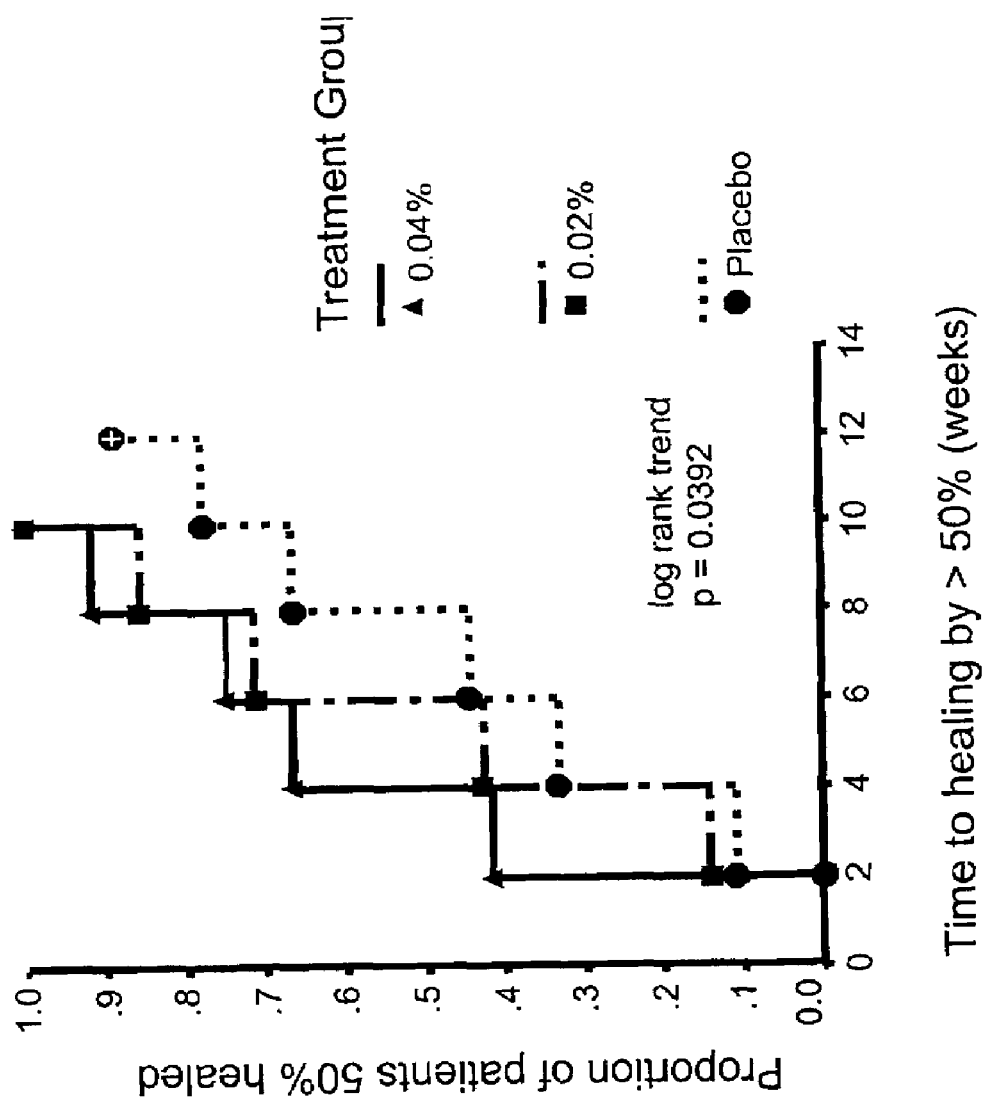
FIG. 2 shows the mean healing times (50%) expressed in survival function plots of Groups 1-3 patients being treated by the compositions of this invention containing different amounts of EGF.
Figure 3:
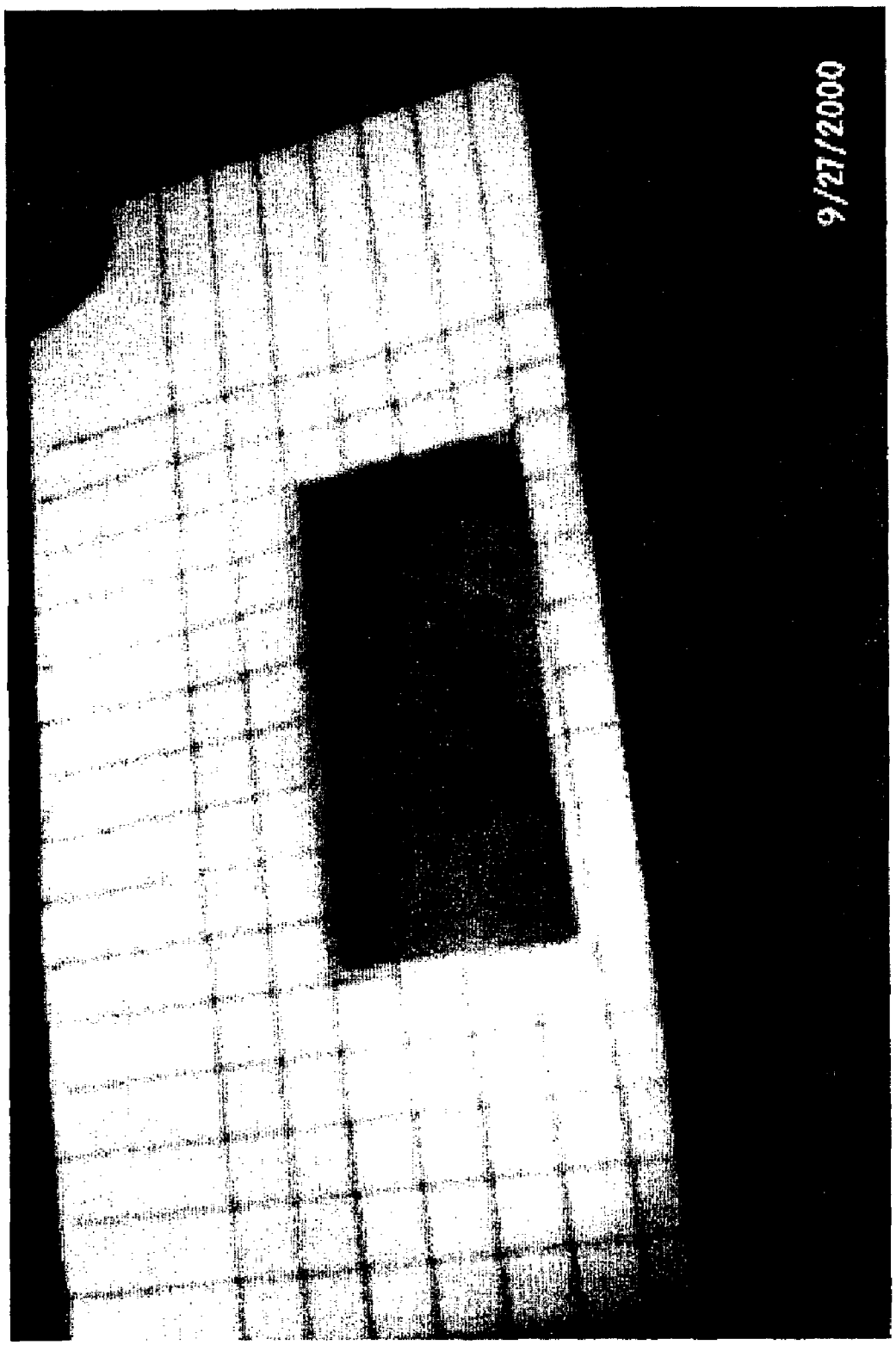
FIG. 3 shows the photo of the wound of Patient A before treatment.
Figure 4:
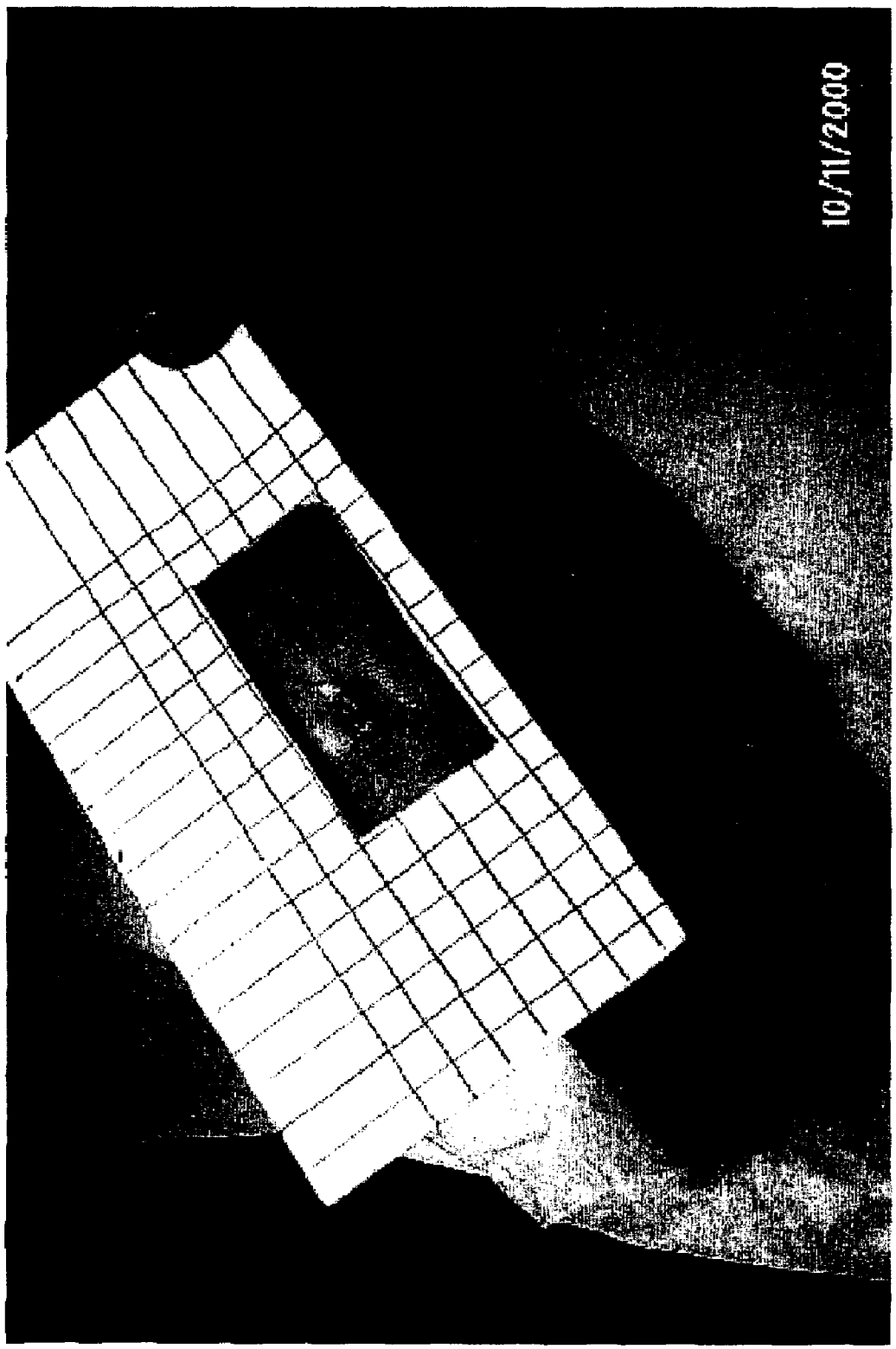
FIG. 4 shows the photo of the wound of Patient A 2 weeks after being treated with the composition of this invention having 0.04% (g/g) of EGF.
Figure 5:
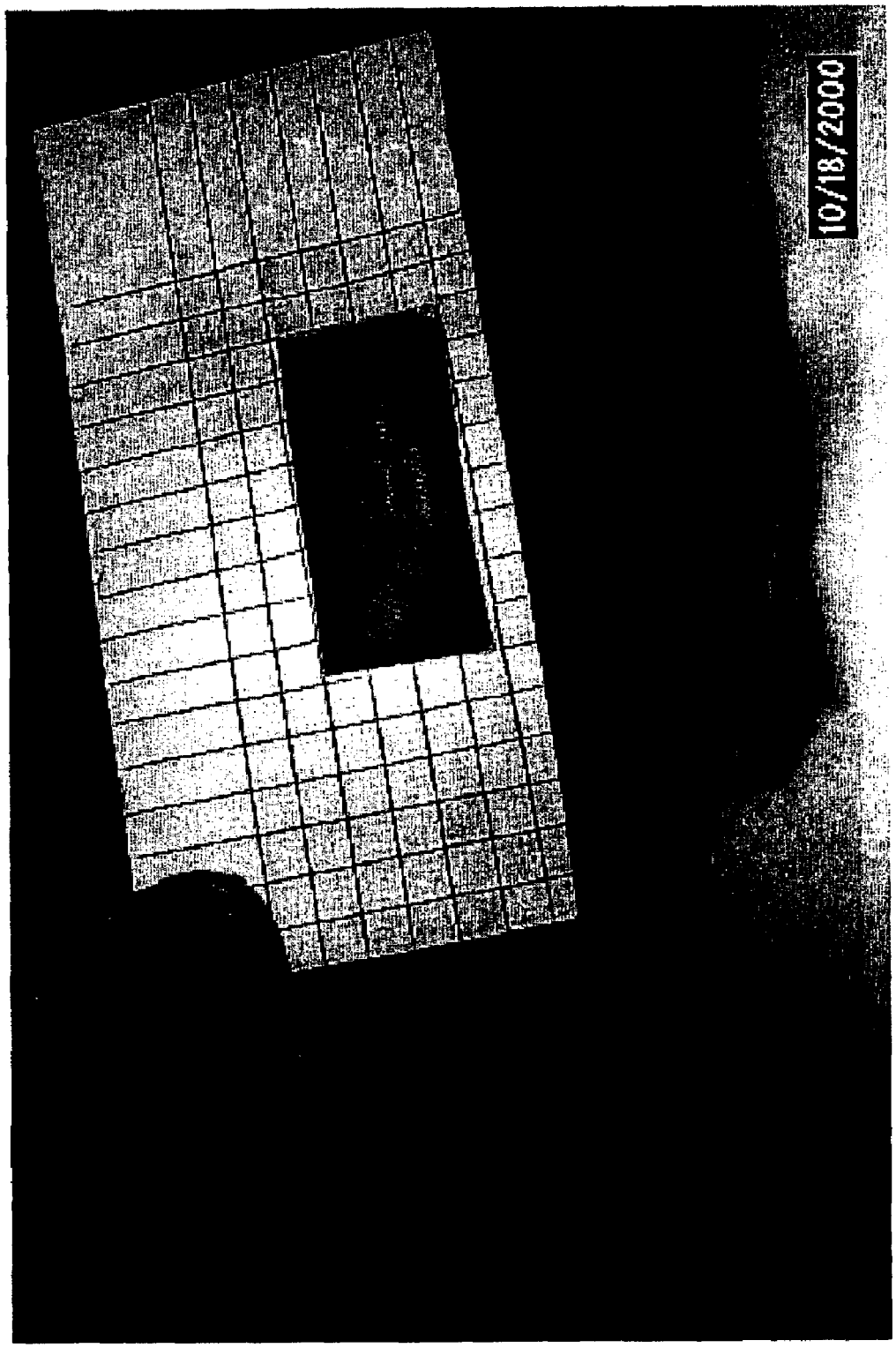
FIG. 5 shows the photo of the wound of Patient A 3 weeks after being treated with the composition of this invention having 0.04% (g/g) of EGF.
Figure 6:
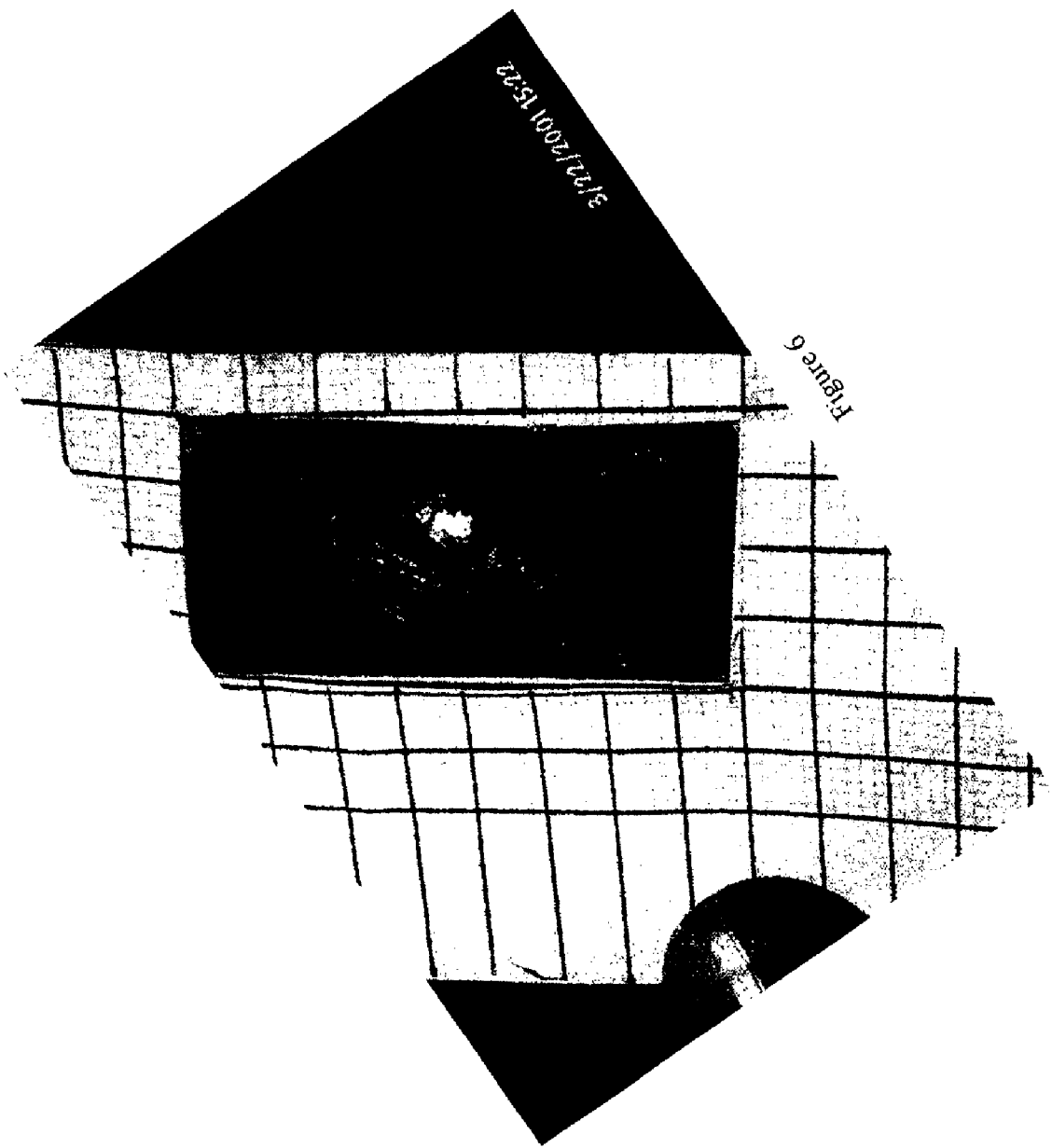
FIG. 6 shows the photo of the wound of Patient B before treatment.
Figure 7:
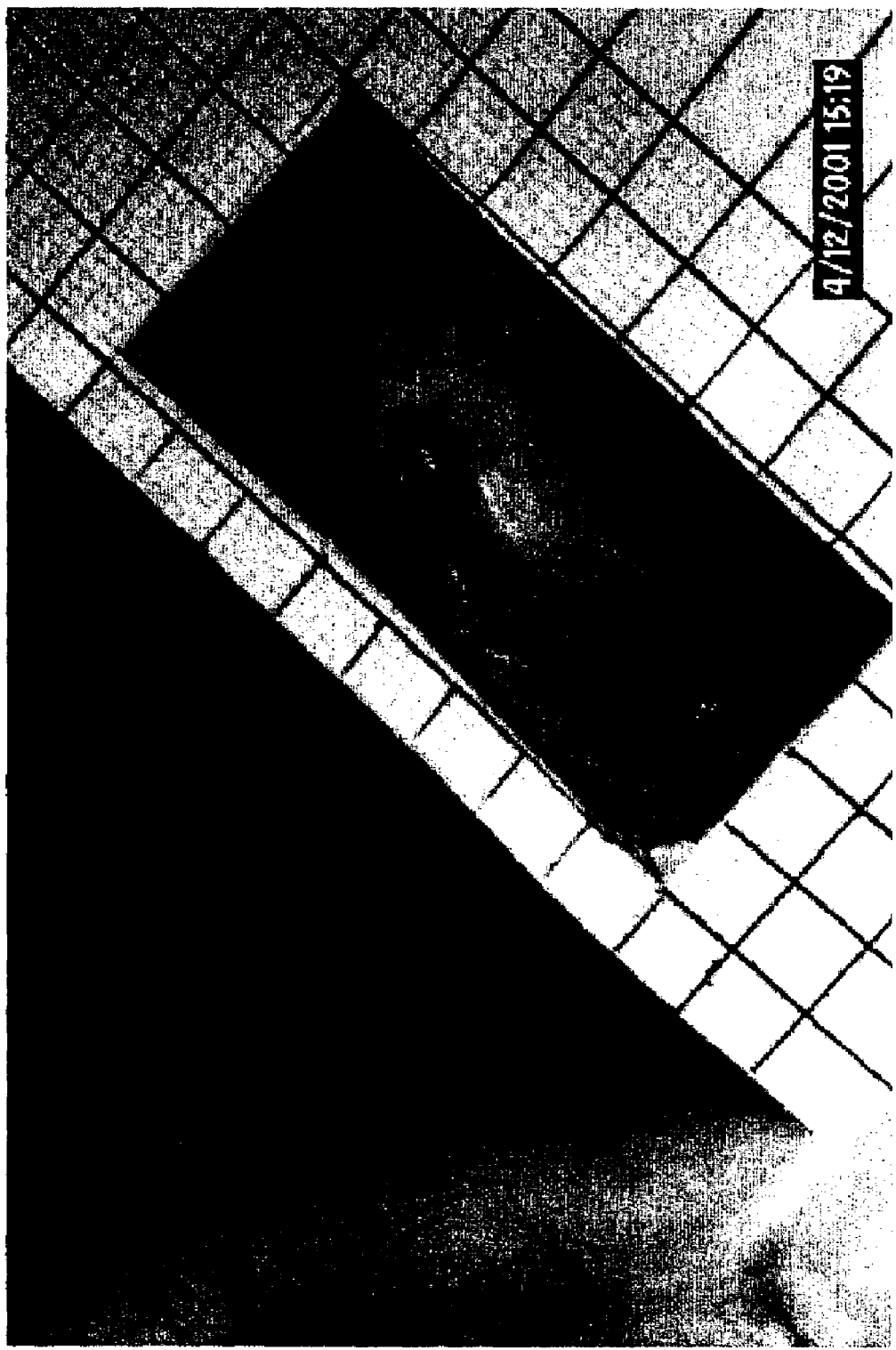
FIG. 7 shows the photo of the wound of Patient B 3 weeks after being treated with the composition of this invention having 0.04% (g/g) of EGF.
Figure 8:
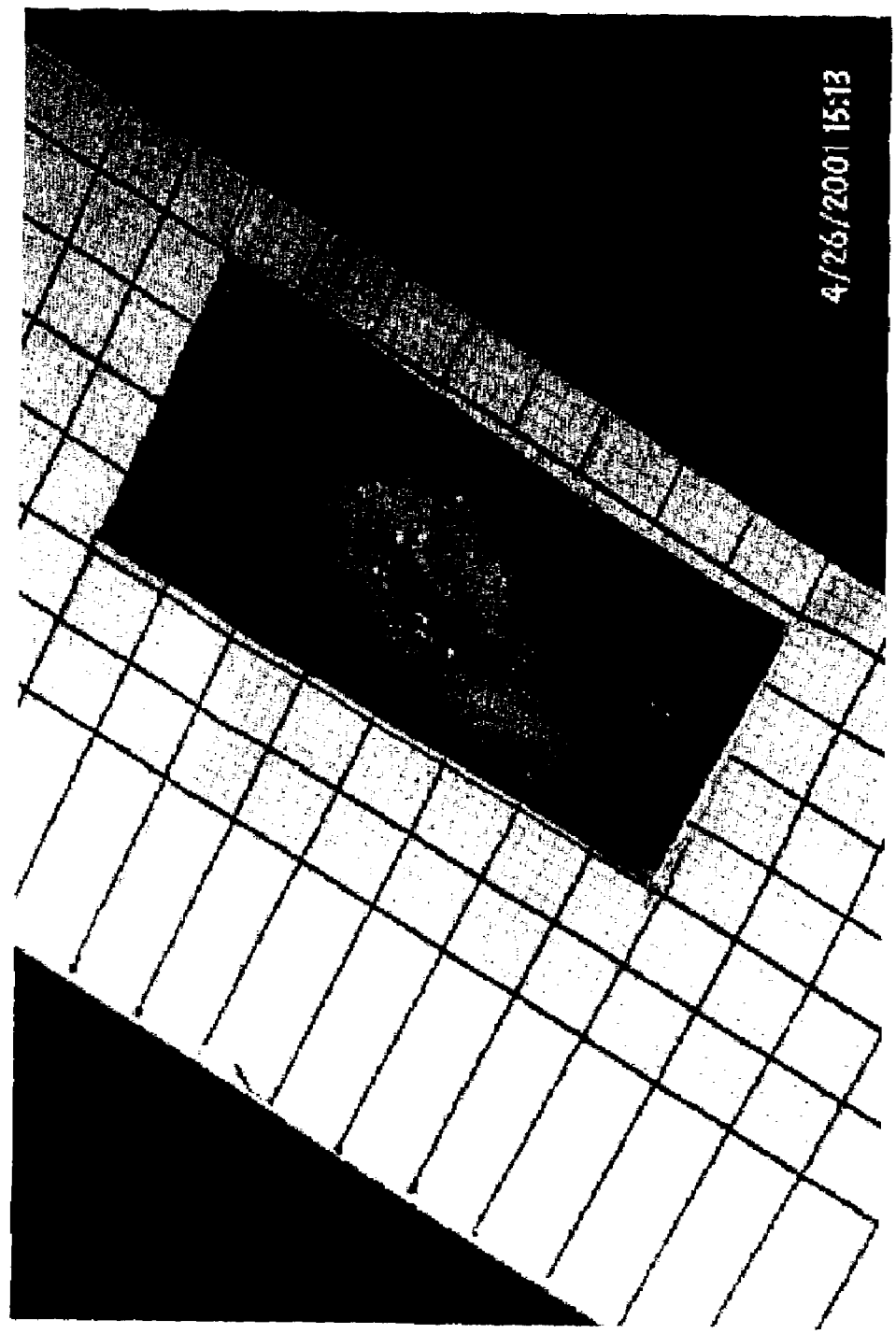
FIG. 8 shows the photo of the wound of Patient B 5 weeks after being treated with the composition of this invention having 0.04% (g/g) of EGF.
Figure 9:
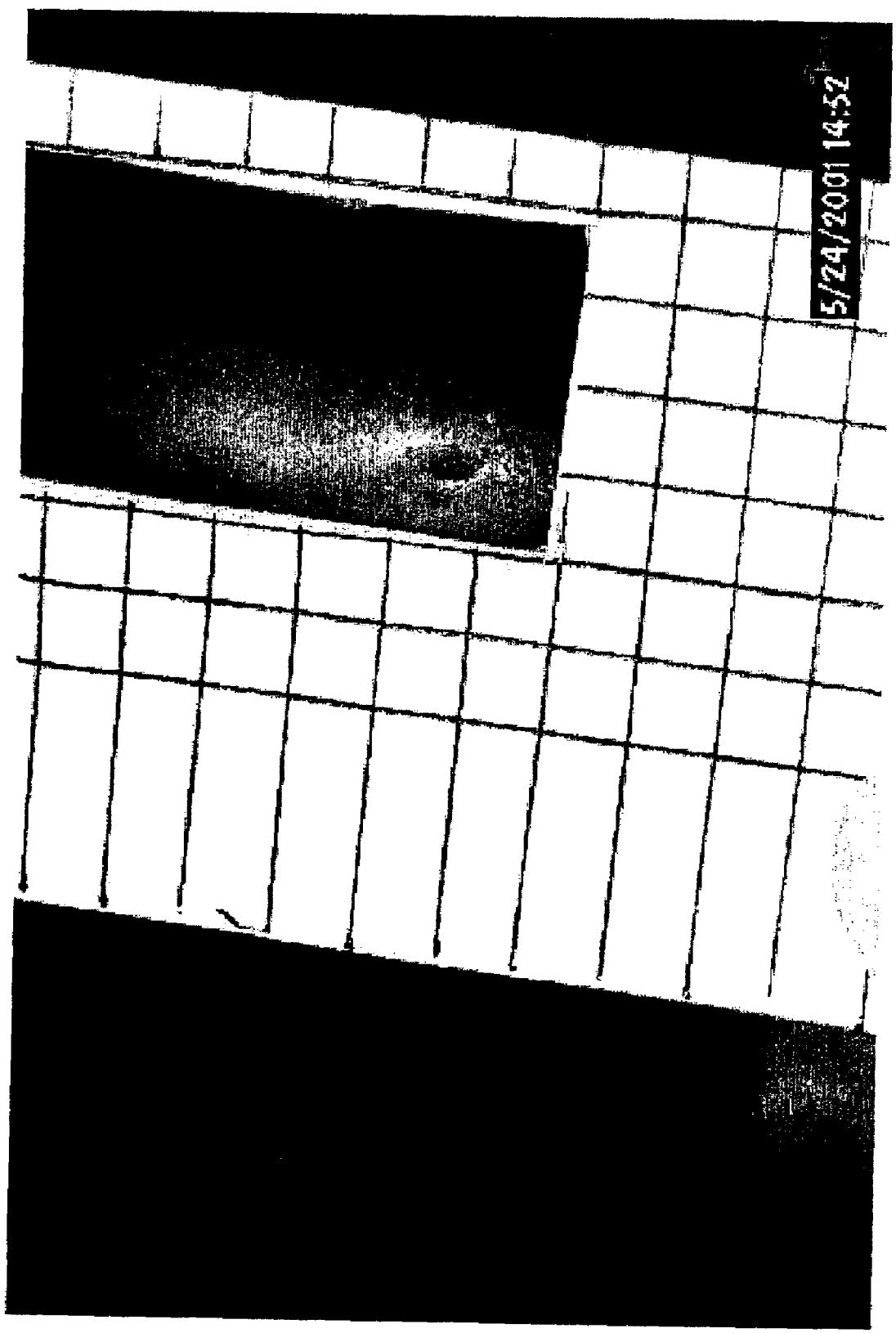
FIG. 9 shows the photo of the wound of Patient B 9 weeks after being treated with the composition of this invention having 0.04% (g/g) of EGF.
Figure 10:
FIG. 10 shows the photo of the wound of Patient C before treatment.
Figure 11:
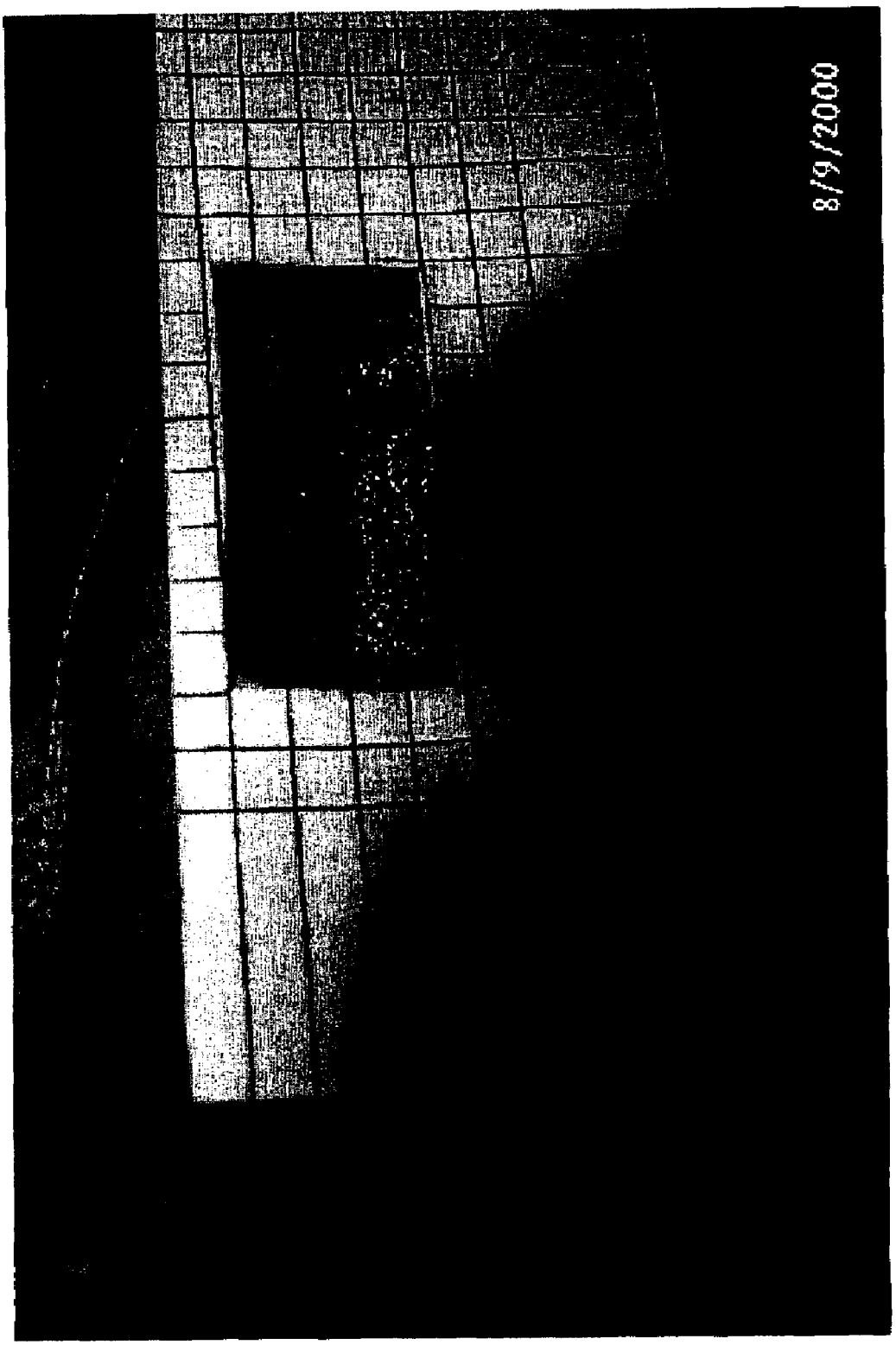
FIG. 11 shows the photo of the wound of Patient C 4 weeks after being treated with the composition of this invention having 0.04% (g/g) of EGF.
Figure 12:
FIG. 12 shows the photo of the wound of Patient C 6 weeks after being treated with the composition of this invention having 0.04% (g/g) of EGF.

FIG. 2 shows the mean 50% healing times in Group 1, Group 2 and Group 3 patients were 7.33±1.21 weeks (confidence interval (C.I.) 4.96-9.71), 5.71±1.02 weeks (C.I. 3.72-7.71) and 4.50±0.82 weeks (C.I.2.89-6.11), respectively. Test statistics for equality of survival distributions (log rank) is 4.25 with a df of 1 and a significance of 0.0392. Further statistical data of FIG. 2 is shown in Table 3. It was shown that there was a trend showing that the time required for an ulcer to reduce in size by 50% was also reduced in Group-3 and Group-2 treated with hEGF, as shown in FIG. 2.

TABLE 1

Baseline characteristics

|  | Group-1 | Group-2 | Group-3 |
|---|---|---|---|
| Number | 7 | 9 | 12 |
| Sex (M/F) | 3/4 | 4/5 | 2/10 |
| Age (year)‡ | 70 ± 5.6 | 66.28 ± 13.04 | 57.42 ± 13.58 |
| Ankle Brachial Index | 1.03 ± 0.22 | 0.99 ± 0.16 | 1.05 ± 0.19 |
| vibration threshold |  |  |  |
| <25 (n) | 5 | 3 | 7 |
| >25 | 2 | 6 | 5 |
| Wound area cm$^2$# | 2.78 ± 82 | 3.48 ± 0.82 | 3.40 ± 1.1 |
| Duration of wound(week) | 7.0 ± 5.48 | 12.78 ± 18.9 | 13.83 ± 16.59 |
| Glycosylated Hemoglobin % | 9.5 ± 1.78 | 8.89 ± 2.05 | 9.12 ± 1.06 |

° Confidence level P = 0.052
Confidence level P = 1

TABLE 2

Survival Analyis for 100% Healed Time (Weeks) of FIG. 1
(Medians of Groups 1 and 2 are limited to 12 weeks)

|  |  | Survival Time | Standard Error | 95% Confidence Interval | |
|---|---|---|---|---|---|
| Group-1 | Mean | 9.78 | 1.24 | 7.35 | 12.21 |
|  | Median | 12.00 | 2.98 | 6.16 | 17.84 |
| Group-2 | Mean | 9.43 | 1.38 | 6.73 | 12.13 |
|  | Median | 12.00 | 5.24 | 1.74 | 22.26 |
| Group-3 | Mean | 6.67 | 0.93 | 4.84 | 8.49 |
|  | Median | 6.00 | 1.71 | 2.65 | 9.35 |

TABLE 3

Survival Analysis for 50% Healed Time (Weeks) of FIG. 2
(Medians of Groups 1 and 2 are limited to 12 weeks)

|  |  | Survival Time | Standard Error | 95% Confidence Interval | |
|---|---|---|---|---|---|
| Group-1 | Mean | 7.33 | 1.21 | 4.96 | 9.71 |
|  | Median | 8.00 | 1.41 | 5.23 | 10.77 |
| Group-2 | Mean | 5.71 | 1.02 | 3.72 | 7.71 |
|  | Median | 6.00 | 1.20 | 3.66 | 8.34 |
| Group-3 | Mean | 4.50 | 0.82 | 2.89 | 6.11 |
|  | Median | 4.00 | 1.09 | 1.87 | 6.13 |

CONCLUSIONS

The data from the above studies revealed that a concentration of 0.04% (g/g) hEGF showed a significant healing effect in the treatment of diabetic foot ulcer. The average healing time for patents treated with this concentration of hEGF is about 6 weeks, which is at least 3 weeks and significantly shorter than that treated with cream base alone and that treated with 0.02% (g/g) hEGF. On the other hand, samples containing hEGF, whether in a concentration of 0.02% (g/g) or 0.04% (g/g), were shown to be able to expedite the healing process of diabetes foot ulcers as judged by a reduced time to attain a reduced wound size by 50%.

Example 2

Individuals Suffering from Diabetes Ulcers

Three patients suffering from prolonged diabetes ulcers were treated with the composition of this invention containing 0.04% (g/g) hEGF. The following results were observed, with all of the patients were healed after as short as four weeks treatment:

I. Patient A

Patient A, a 72-year old lady, suffered from type 2 diabetes (grade 1) for three years. Eye complication and normal vibration threshold test also presented on oral medication.

| Description of FIGURE | FIG. | Ulcer Area ($cm^2$) | Healing Rate (%) |
|---|---|---|---|
| Before treatment | 3 | 1.60 | — |
| After 2 weeks treatmeat | 4 | 1.02 | 36.25 |
| After 3 weeks treatment | 5 | 0 | 100 |

II. Patient B

Patient B, a 68-year old lady, suffered from type 2 diabetes (grade 1) for a 8 years. Both eye and kidney complication, and borderline vibration threshold test presented.

| Description of FIGURE | FIG. | Ulcer Area ($cm^2$) | Healing Rate (%) |
|---|---|---|---|
| Before treatment | 6 | 6.67 | — |
| After 3 weeks treatment | 7 | 3.79 | 43.18 |
| After 5 weeks treatment | 8 | 1.62 | 75.71 |
| After 9 weeks treatment | 9 | 0.16 | 97.60 |

I. Patient C

Patient C, a 46-year old lady, suffered form type 2 diabetes (grade 1) with no major complication.

| Description of FIGURE | FIG. | Ulcer Area ($cm^2$) | Healing Rate (%) |
|---|---|---|---|
| Before treatment | 10 | 13.23 | — |
| After 4 weeks treatment | 11 | 1.41 | 89.34 |
| After 6 weeks treatment | 12 | 0 | 100 |

Example 3

Individual Suffering from Prolonged Unhealed Surgical Wound

Patient D, aged 50, was admitted for investigation of right facial non-healing ulcer after extraction of right mandibular molars and excision of facial fistula eleven months ago. The facial ulceration increased in and with tendency of superior erosion. There was sloughing of the right mandibular alveolus and the wound was tender.

Blood tests, histopathology and microbiology revealed no specific cause for the non-healing wound. Repeated biopsy and microbiological investigations revealed no specific diagnosis. However, "definitively negative finding for malignancy nor basal cell carcinoma, quite normal looking oral epithelial mucosa" was reported by a pathologist. Computerized tommogram scanning of the face revealed a right facial ulcer deep to the facial muscle with no bony lesion. A bone scan done revealed hot uptake of the whole mandible.

Figure 13:
FIG. 13 shows the photo of the wound of Patient D before treatment.
Figure 14:
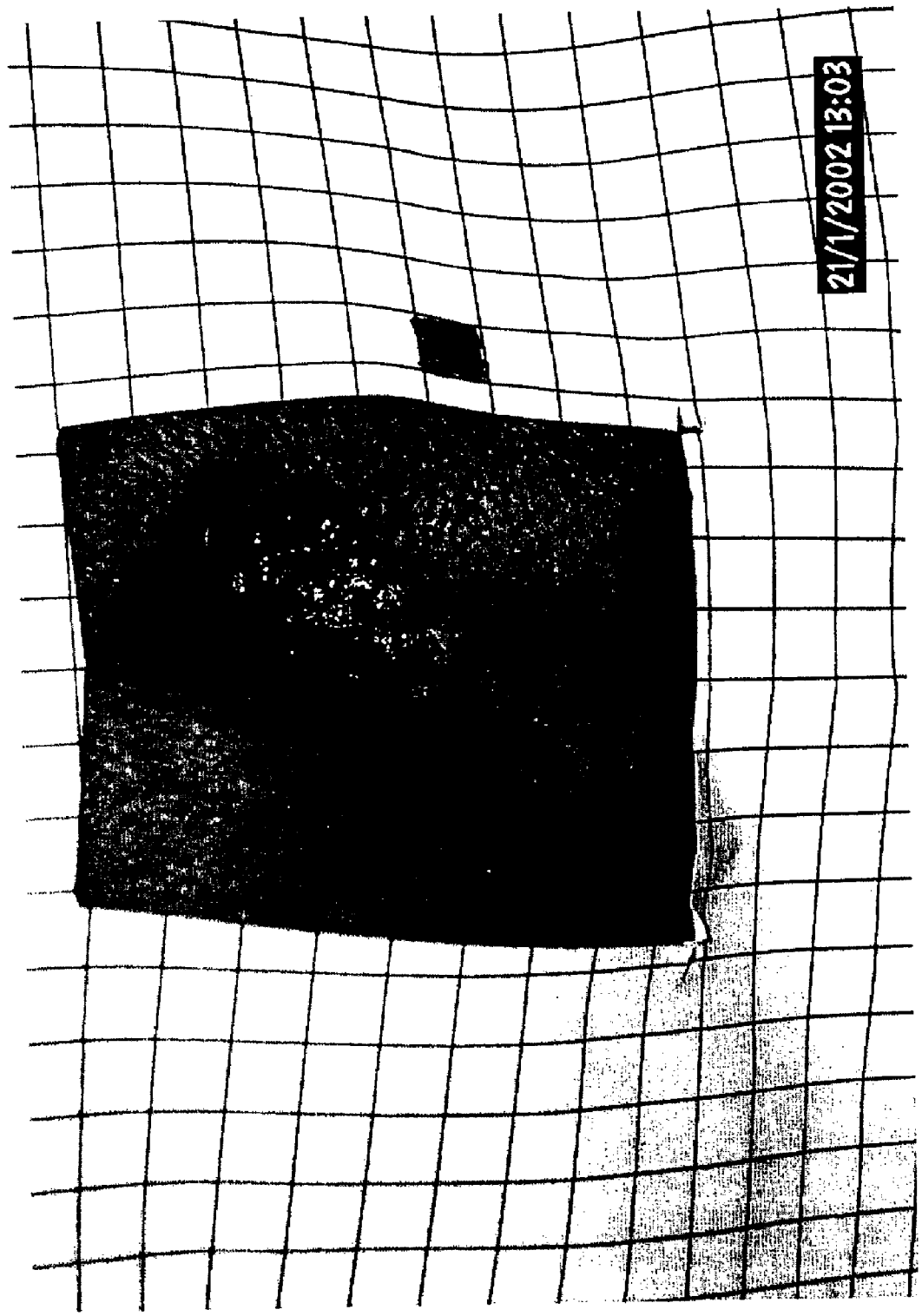
FIG. 14 shows the photo of the wound of Patient D 2 weeks after being treated with the composition of this invention having 0.04% (g/g) of EGF.
Figure 15:
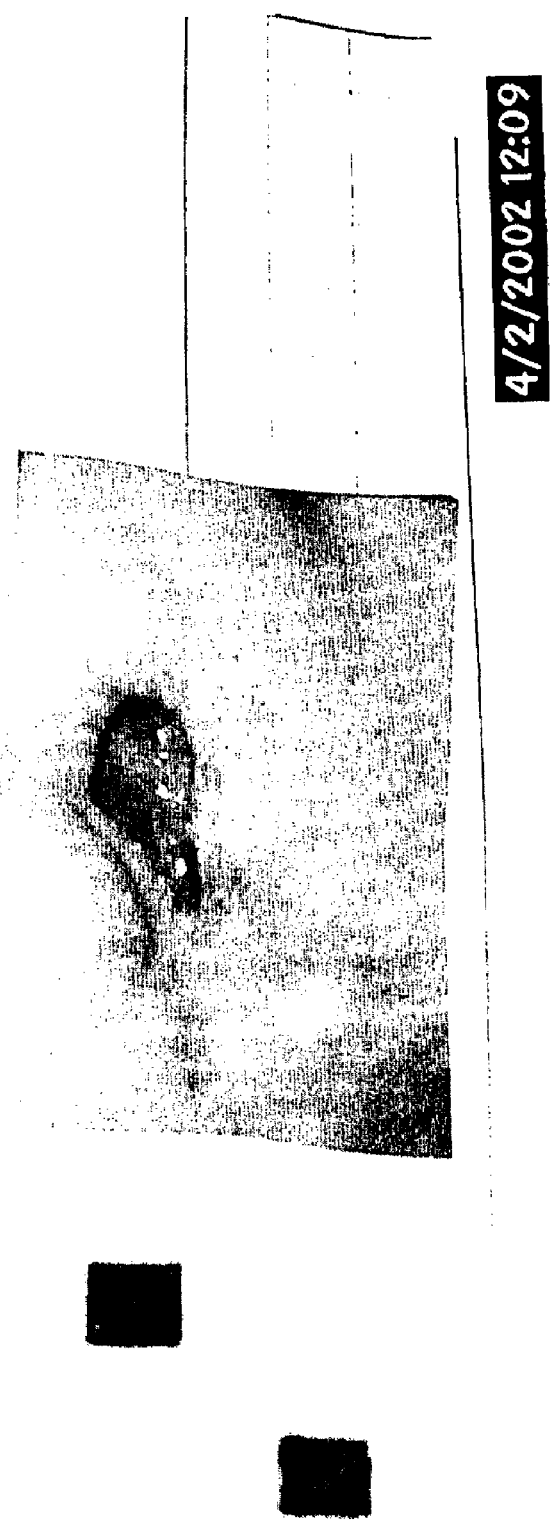
FIG. 15 shows the photo of the wound of Patient D 4 weeks after being treated with the composition of this invention having 0.04% (g/g) of EGF.
Figure 16:
FIG. 16 shows the photo of the wound of Patient B before treatment
Figure 17:
FIG. 17 shows the photo of the wound of Patient E 5 weeks after being treated with the composition of this invention having 0.04% (g/g) of EGF.
Figure 18:
FIG. 18 shows the photo of the wound of Patient B 9 weeks after being treated with the composition of this invention having 0.04% (g/g) of EGF.

Patient was reviewed after two weeks of hEGF (0.04% (g/g)) local application. The composition is the same as that used in the above Group-3 patients. The right facial wound was healing, base of the wound looked fleshy with no discharge. The wound area decreased in size by about 30%. Further reduction in size was noted in subsequent follow up. The progress can be seen in FIGS. 13-15, in which FIG. 13 shows the photo of the wound of Patient A before treatment; FIG. 14 shows the photo of the wound of Patient A 2 weeks after being treated with the composition of this invention having 0.04% (g/g) of EGF; and FIG. 15 shows the photo of the wound of Patient A 5 weeks after being treated with the composition of this invention having 0.04% (g/g) of EGF.

In conclusion, after 5 weeks of 0.04% of epidermal growth factor (hEGF) applied locally the refractroy facial wound achieved a approximately 50% reduction in size and decrease in wound depth.

Example 4

Individuals Suffering from Bedsore

Patient E, aged 82, was bedridden at aged home for several years. She was found to have pemphoid because of generalized blister eruptions and has been on tailing dose of prednisone for more than 8 months. She was referred to medical because the wound got worse with central grangrene after a two-month treatment.

She was then treated with Hibitane dressing for two weeks then normal saline dressing with the composition of this invention containing 0.04% (g/g) EGF daily. Her wound was healed and completely closed after three-month treatment.

| Description of FIGURE | FIG. |
|---|---|
| Before treatment | 16 |
| After 5 weeks treatment | 17 |
| After 9 weeks treatment | 18 |

Example 5

Results of 0.03% a (g/g) EGF

The experiment in Example 1 was repeated using Acetovegin® 5% cream plus 0.03% (g/g) hEGF. 8 patients, named Group-4, were treated. The results are shown as follows:

| Time (weeks) | Status | Cumulative Survival | Standard Error | Cumulative Events | Number Remaining |
|---|---|---|---|---|---|
| 2 | heal | 0.8750 | 0.1169 | 1 | 7 |
| 4 | heal | | | 2 | 6 |
| 4 | heal | 0.6250 | 0.1712 | 3 | 5 |
| 6 | heal | 0.5000 | 0.1768 | 4 | 4 |
| 8 | heal | 0.3750 | 0.1712 | 5 | 3 |
| 10 | heal | 0.2500 | 0.1531 | 6 | 2 |
| 12 | heal | 0.1250 | 0.1169 | 7 | 1 |
| 12 | not heal | | | 7 | 0 |

Number of Cases: 8 Censored: 1 (12.50%) Events: 7

| | | 95% Confidence |
| Survival Time | Standard Error | Level |

| -continued | | | |
|---|---|---|---|
| Mean (Limited to 12) | 7 | 1 | (5, 10) |
| Median | 6 | 3 | (0, 12) |

Figure 19:
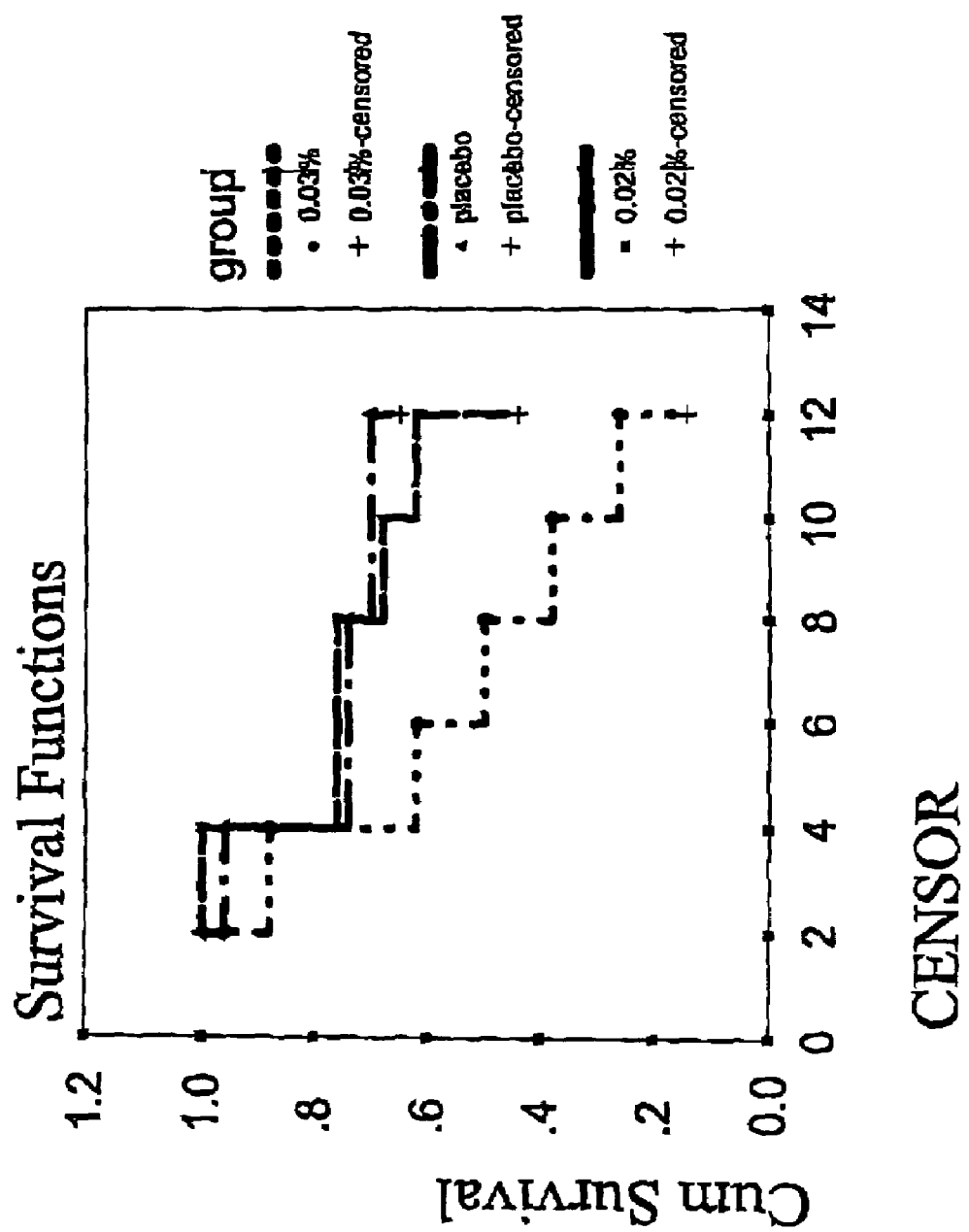
FIG. 19 shows the mean healing times (100% healing) expressed in survival function plots of Group 4 patients being treated by the compositions of this invention containing 0.03% (g/g) EGF and comparing with Groups 1 and 2 patients.

FIG. 19 shows the mean 100% healing times in Group 1, Group 2 (from results in Example 1 above) and Group-4 patients were 9.79±1.24 weeks (confidence interval (C.I.) 7.35-12.21), 9.43±1.38 weeks (C.I. 6.73-12.13) and 7 weeks (C.I.5-10), respectively. Test statistics for equality of survival distributions (log rank) is 6.79 with a df of 2 and a significance of 0.0366. It can be observed that Group-4 patients treated with 0.03% (g/g) (7 weeks) EGF healed almost as fat as those tread with 0.04% (g/g) EGF (6.67 weeks) with no substantial statistical difference.

It can be seen that this invention may have provided a relatively effective treatment to serious, prolonged and unhealed skin wounds from the above examples. Such skin wounds can result from diabetes foot ulcers, bedsores, or surgical wounds. At the very least, this invention may have provided a solution to such skin wounds that traditional treatment methods may fail to heal. Further, the period required for total healing can be relatively short, and only 2-4 weeks may be required in some cases, while other more severe wounds may require up to 8 weeks.

While the preferred embodiment of the present invention has been described in detail by the examples, it is apparent that modifications and adaptations of the present invention will occur to those skilled in the art. It is to be expressly understood, however, that such modifications and adaptations are within the scope of the present invention, as set forth in the following claim. Furthermore, the embodiments of the present invention shall not be interpreted to be restricted by the examples or figures only.

The invention claimed is:

1. A method for treating a diabetic foot ulcer or bedsore wound comprising the steps of:
    performing debridement to the skin wound; and
    topically applying a composition to the skin wound,
        wherein said composition comprises a topically acceptable carrier and at least 0.03% by weight of epidermal growth factor (EGF) wherein said EGF is effective at treating the wound.

2. The method of claim 1, wherein the EGF is a human epidermal growth factor (hEGF).

3. The method of claim 1, wherein a topically effective amount of EGF is at least 0.04% by weight.

4. The method of claim 1, wherein the EGF is a human epidermal growth factor (hEGF) and the composition comprises 0.03% to 0.04% by weight of hEGF.

5. The method of claim 1 further comprising the steps of:
    (a) topically administering said composition including 0.03% by weight of hEGF to the skin wound until area of the skin wound is reduced by 50%; and
    (b) topically administering said composition including 0.04% by weight hEGF to the skin wound after area of the skin wound is reduced by 50% until the skin wound is totally healed.

6. The method of claim 1, wherein the topically acceptable carrier is a water-miscible carrier.

7. The method of claim 1, wherein the topically acceptable carrier includes a constituent selected from the group consisting of water, petroleum jelly, petrolatum, mineral oil, vegetable oil, animal oil, wax, and a polymer.

\* \* \* \* \*